United States Patent
Tomoe

(10) Patent No.: US 8,396,186 B2
(45) Date of Patent: Mar. 12, 2013

(54) DENTAL X-RAY PHOTOGRAPHING DEVICE

(75) Inventor: Takeshi Tomoe, Tokyo (JP)

(73) Assignee: The Yoshida Dental Mfg. Co., Ltd., Sumida-ku, Tokyo (JP)

(*) Notice: Subject to any disclaimer, the term of this patent is extended or adjusted under 35 U.S.C. 154(b) by 0 days.

(21) Appl. No.: 13/497,211

(22) PCT Filed: Sep. 14, 2010

(86) PCT No.: PCT/JP2010/065831
§ 371 (c)(1),
(2), (4) Date: Mar. 20, 2012

(87) PCT Pub. No.: WO2011/037044
PCT Pub. Date: Mar. 31, 2011

(65) Prior Publication Data
US 2012/0183120 A1    Jul. 19, 2012

(30) Foreign Application Priority Data
Sep. 28, 2009   (JP) .................................. 2009-223269

(51) Int. Cl.
*A61B 6/14*    (2006.01)
(52) U.S. Cl. .......................................... 378/39
(58) Field of Classification Search .................. 378/38, 378/39, 62, 193, 196, 197
See application file for complete search history.

(56) References Cited

U.S. PATENT DOCUMENTS
5,692,507 A   12/1997  Seppi et al.
6,055,292 A    4/2000  Zeller et al.
(Continued)

FOREIGN PATENT DOCUMENTS
DE   103 13 109   10/2004
EP   1 219 244    7/2002
(Continued)

OTHER PUBLICATIONS
International Search Report for International Application No. PCT/JP2010/065831 mailed Nov. 2, 2010 (English translation provided).
(Continued)

*Primary Examiner* — Irakli Kiknadze
(74) *Attorney, Agent, or Firm* — Merchant & Gould P.C.

(57) ABSTRACT

A dental x-ray photographing device includes a rotating means (3) for rotating an arm (2) which supports an x-ray source (11) and an x-ray imaging means (12), a sliding means (4) for linearly moving the x-ray imaging means (12). The dental x-ray photographing device obtains a first set of projection images which goes through a first region by moving the x-ray imaging means (12) to a first detection position, obtains a second set of projection images which goes through a second region by moving the x-ray imaging means (12) to a second detection position, and paste the first set of projection images and the second set of projection images together. An origin-position detecting means (5) for detecting an origin position of the x-ray imaging means (12) includes an optical sensor (52) that detects a position of an end (51a) of a light blocking plate that linearly moves together with the x-ray imaging means (12), and detects a time point at which the end (51a) of the light blocking plate passes the optical sensor (52) in the forward direction as the origin position. According to such a configuration, it becomes possible to obtain a highly precise and large FOV using the x-ray imaging means that has a narrow photo receiving surface.

4 Claims, 12 Drawing Sheets

U.S. PATENT DOCUMENTS

| | | | |
|---|---|---|---|
| 6,118,171 A * | 9/2000 | Davies et al. | 257/586 |
| 6,219,401 B1 * | 4/2001 | Tachibana et al. | 378/39 |
| 6,519,314 B1 | 2/2003 | Baba et al. | |
| 6,584,171 B2 * | 6/2003 | Suzuki et al. | 378/98.8 |
| 7,322,746 B2 | 1/2008 | Beckhaus et al. | |
| 7,486,767 B2 * | 2/2009 | Sonobe et al. | 378/39 |
| 7,559,692 B2 | 7/2009 | Beckhaus et al. | |
| 7,773,720 B2 * | 8/2010 | Honjo et al. | 378/19 |
| 8,005,187 B2 | 8/2011 | Suzuki et al. | |
| 2004/0258195 A1 | 12/2004 | Hara | |

FOREIGN PATENT DOCUMENTS

| | | |
|---|---|---|
| JP | 5-502399 | 4/1993 |
| JP | 9-327453 | 12/1997 |
| JP | 11-9583 | 1/1999 |
| JP | 2000-5154 | 1/2000 |
| JP | 2002-263094 | 9/2002 |
| JP | 2005-6772 | 1/2005 |
| JP | 2005-37158 | 2/2005 |
| JP | 2005-527800 | 9/2005 |
| JP | 2006-320347 | 11/2006 |
| JP | 2007-144137 | 6/2007 |
| JP | 2007-159987 | 6/2007 |
| WO | WO 03/081220 | 10/2003 |
| WO | WO 2007/046372 | 4/2007 |

OTHER PUBLICATIONS

German Office Action for Application No. 11 2010 003 822.8 mailed Nov. 5, 2012.

* cited by examiner

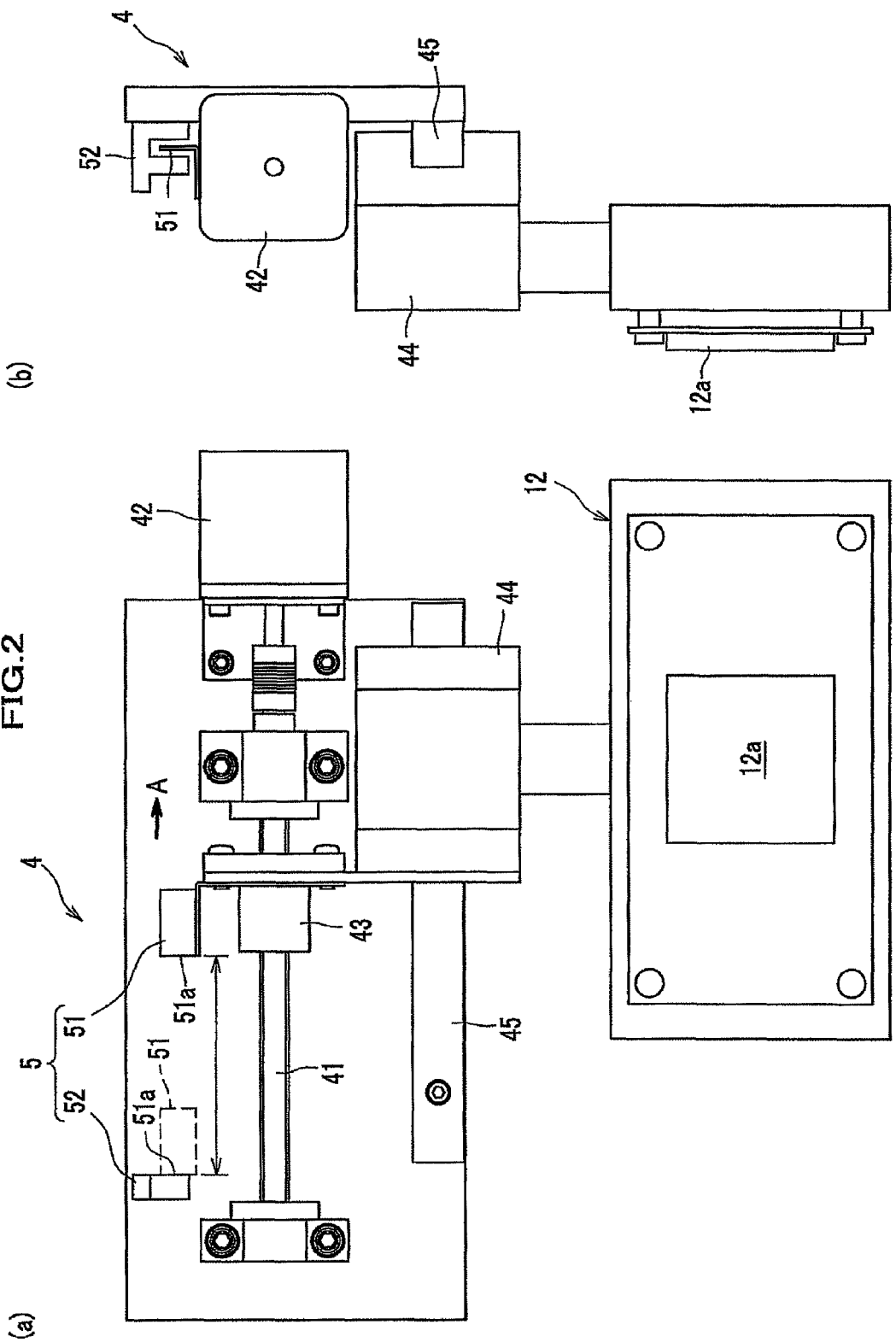

FIG.3A
(a)
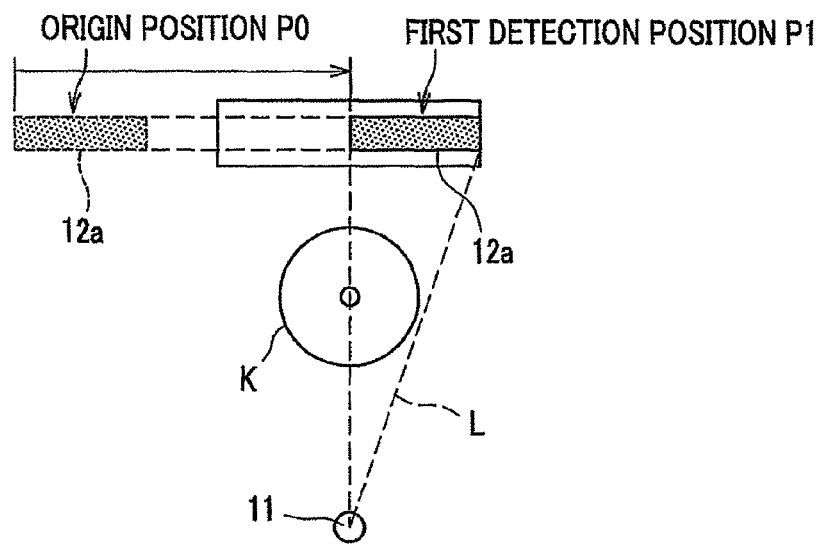
(b)
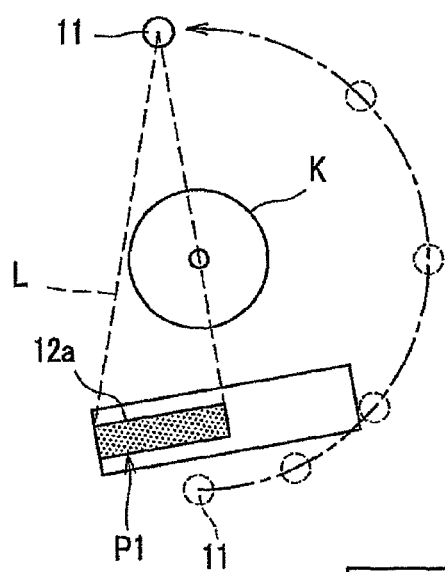
(c)
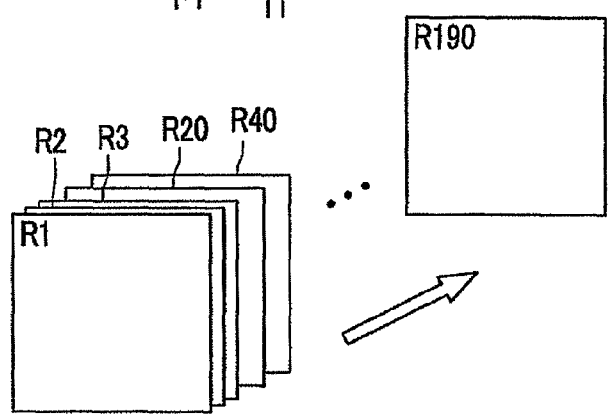

FIG.3B
(a)
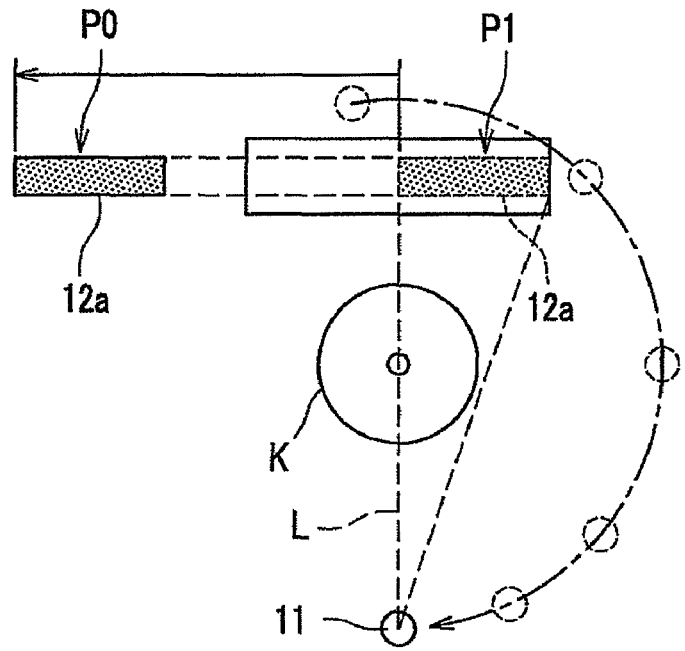
(b)
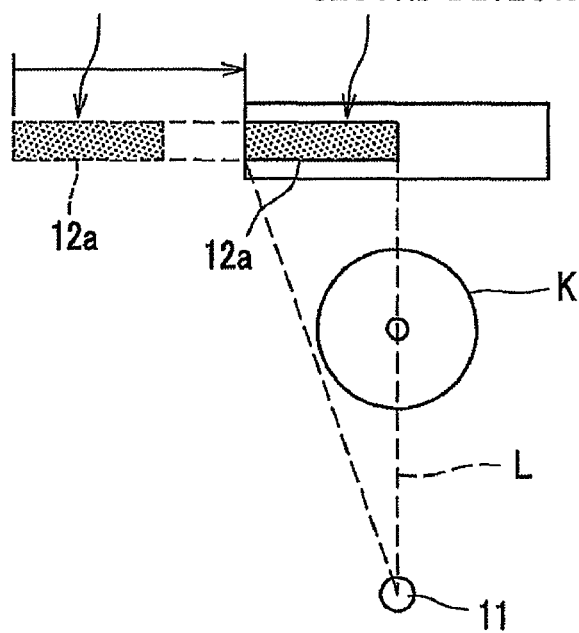

FIG.3C
(a)
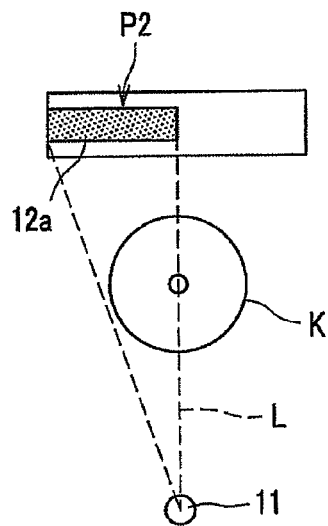
(b)
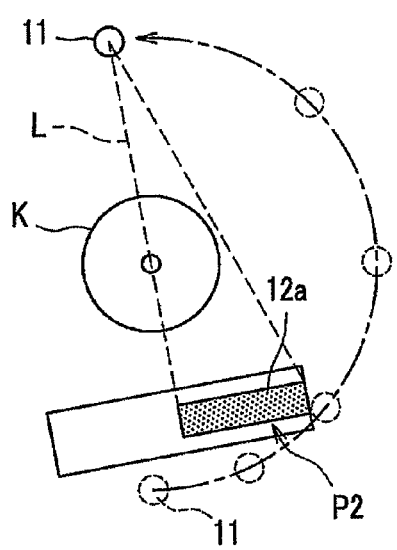
(c)
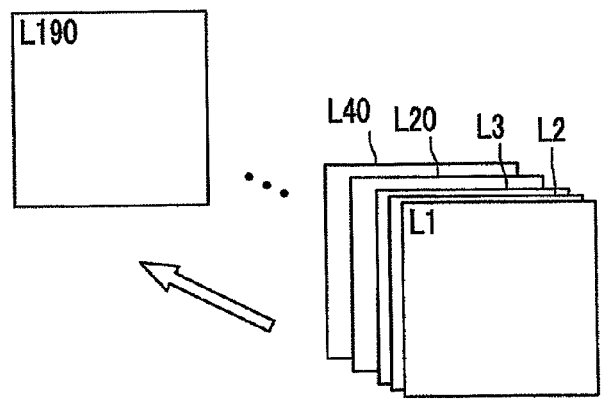

FIG.4A
(a) 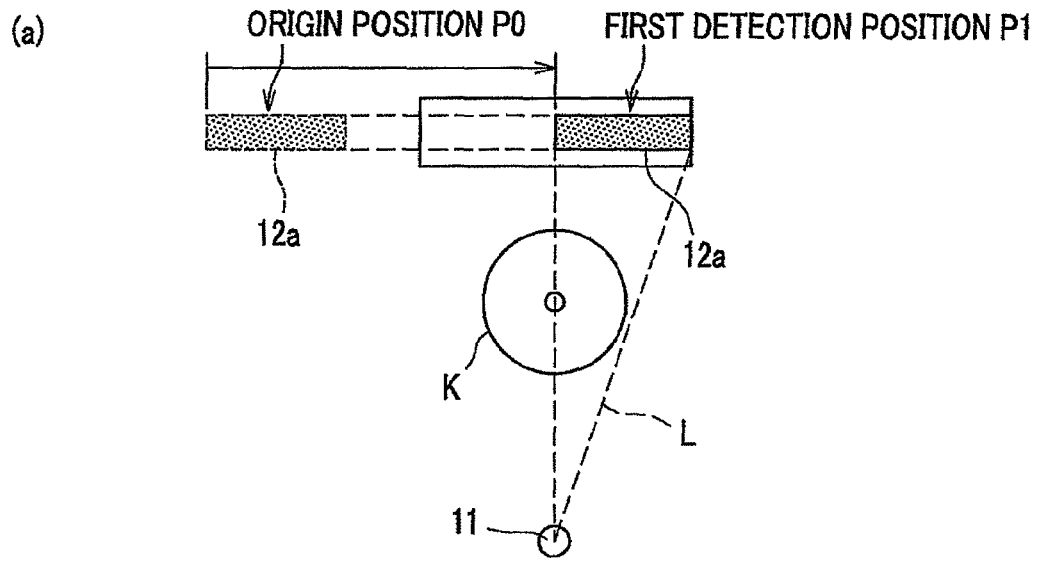
(b) 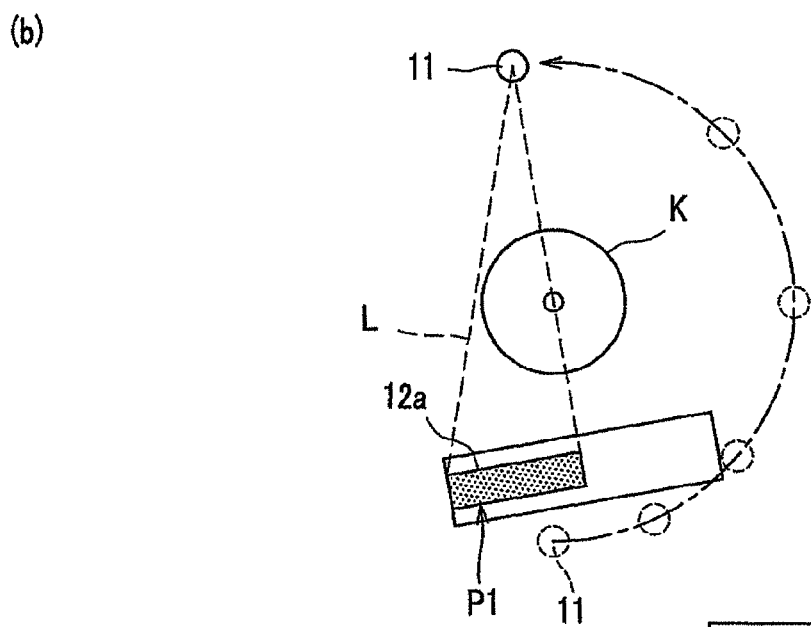
(c) 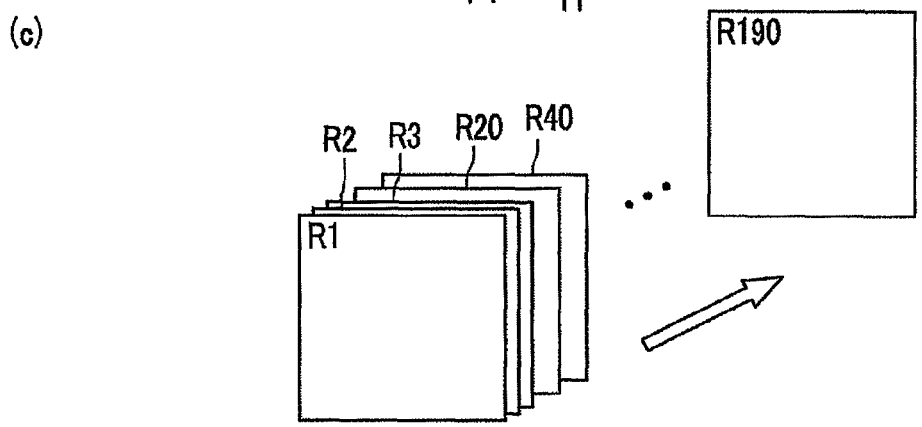

FIG.4B
(a)
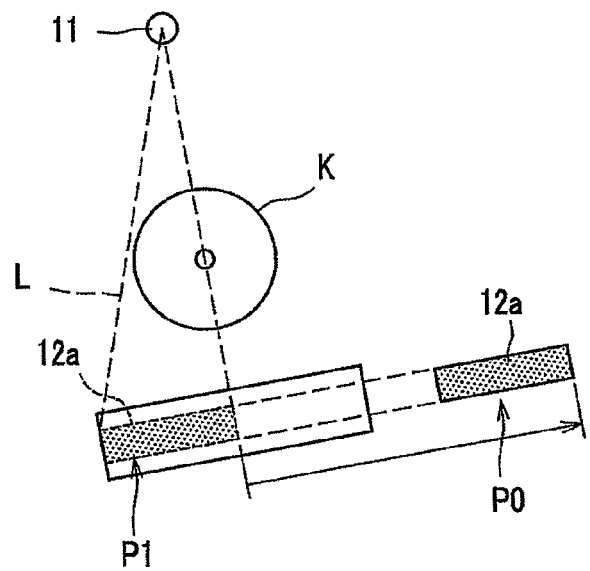
(b)
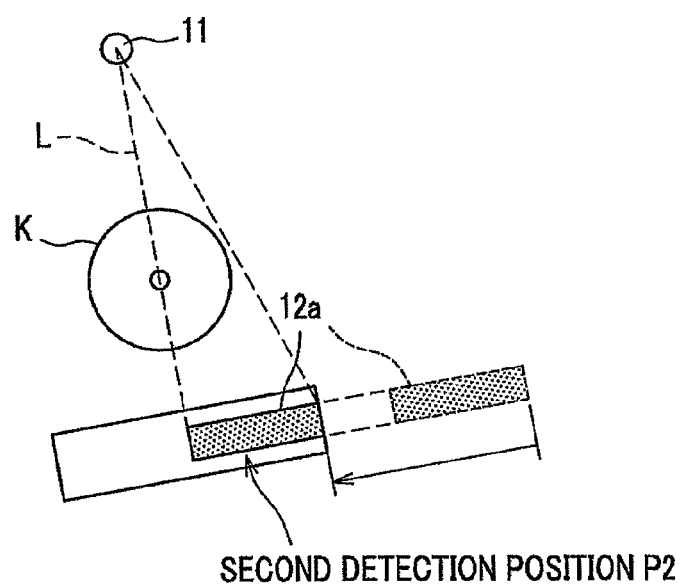
SECOND DETECTION POSITION P2

FIG.4C
(a)
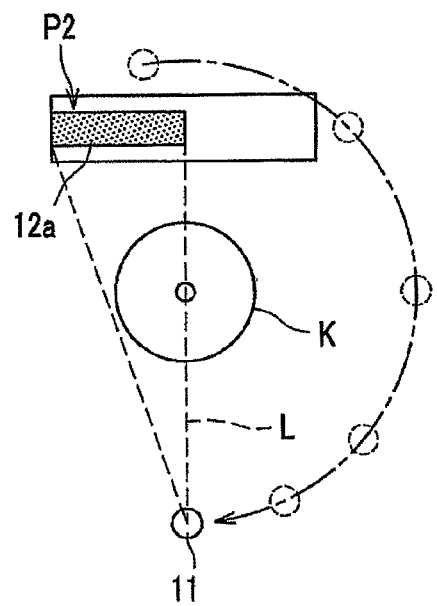
(b)
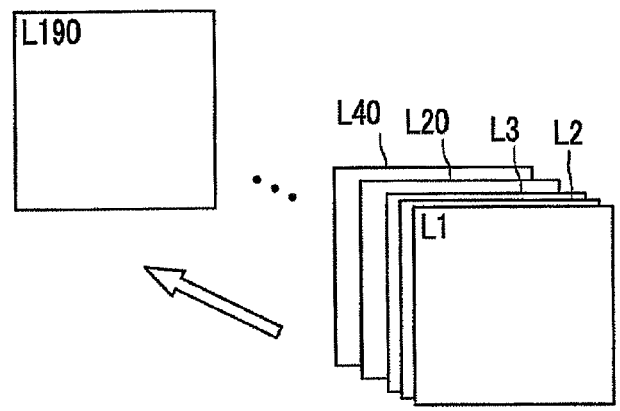
(c)
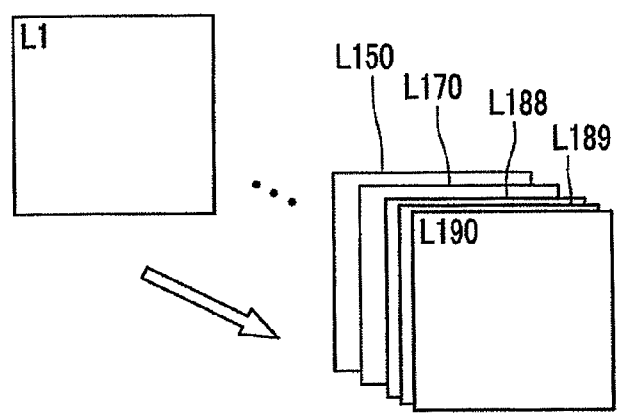

FIG.5
(a)
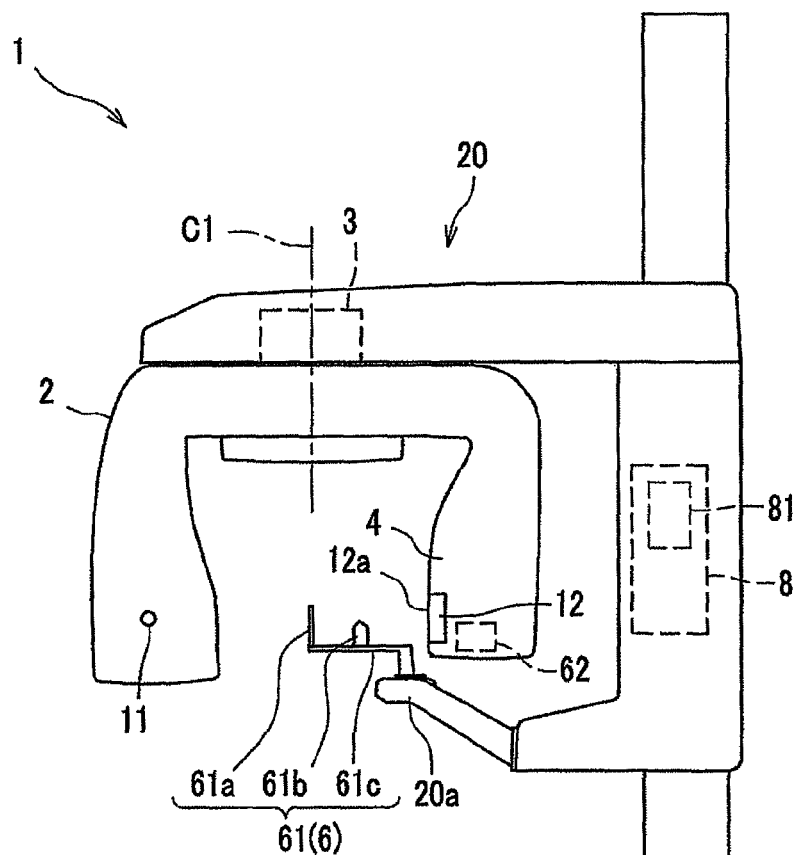
(b)
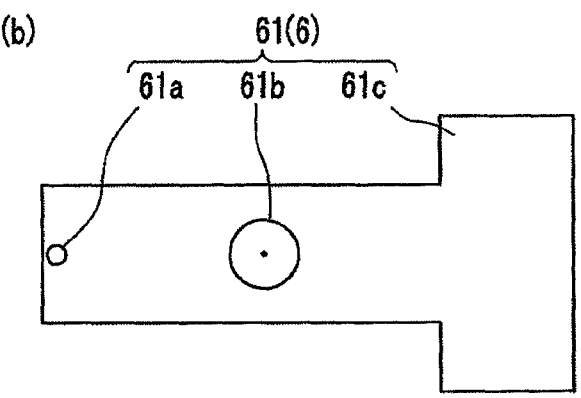

DENTAL X-RAY PHOTOGRAPHING DEVICE

This application is a National Stage Application of PCT/JP2010/065831, filed 14 Sep. 2010, which claims benefit of Serial No. 2009-223269, filed 28 Sep. 2009 in Japan and which applications are incorporated herein by reference. To the extent appropriate, a claim of priority is made to each of the above disclosed applications.

TECHNICAL FIELD

The present invention relates to a dental x-ray photographing device, and in particular, a dental x-ray photographing device which linearly moves an x-ray imaging means in a direction along a photo receiving surface and pastes and composes projection images together, which projection images are obtained at respective positions.

BACKGROUND ART

Conventionally, a CT photographing (a computed tomographing) device in dental treatment obtains an FOV (Field Of View) which is set based on a size of a photo receiving surface and a mechanical geometry (an x-ray source, the center of rotation, and a geometrical arrangement of the photo receiving surface).

Also, a technique is known which is for obtaining a large FOV (field of view) by pasting projection images together in the case of an x-ray fluoroscopic photographing device (see Patent Literature 1).

PRIOR ART DOCUMENTS

Patent Literature

Patent Literature 1: JP 2002-263094 A (see FIGS. 5 and 7)

DISCLOSURE OF INVENTION

Problem to be Solved by the Invention

However, the larger the size of the photo receiving surface is, the more expensive an x-ray imaging means which is needed for a CT photographing becomes, so that a cost increases when the photo receiving surface is enlarged in order to obtain a larger FOV. Also, the size of a processing device for image data increases and the device becomes expensive as a whole, so that a CT photographing device that has a large FOV does not come in wide use in dental treatment.

On the other hand, it is necessary for the dental x-ray photographing device to obtain a highly precise tomographic image, so that when it is attempted to obtain a large FOV by pasting the projection images together, the precision of pasting may become a technical issue. For example, according to the technique described in Patent Literature 1, it is difficult to secure the movement precision of the x-ray imaging means since the x-ray imaging device is moved along an arcuate guide rail, and a data processing becomes complex.

In order to overcome the problem described above, it is an object of the present invention to provide a dental x-ray photographing device that is capable of obtaining a highly precise image while at the same time obtaining a large FOV using an inexpensive x-ray photographing means that has a small photo receiving surface.

Means for Solving the Problem

In order to overcome the above problems, the present invention provides a dental x-ray photographing device that includes an x-ray source that emits x-ray beam to an object, an x-ray imaging means for detecting the x-ray beam which is emitted from the x-ray source and passes through the object, a supporting means for supporting the x-ray source and the x-ray imaging means, a rotating means for rotating the supporting means around a vertical axis to rotate the x-ray source and the x-ray imaging means around the object in a horizontal direction, a sliding means for linearly moving the x-ray imaging means in a direction along a photo receiving surface, a control device that controls an operation of the rotating means and an operation of the sliding means, and an image processing means for processing a projection image which is obtained by the x-ray imaging means, in which the control device executes a first sliding step of causing the sliding means to move the x-ray imaging means to a first detection position where the x-ray beam that passes through a first region of the object is detected, a first imaging step of causing the x-ray imaging means to obtain a first set of projection images which go through the first region while the x-ray source and the x-ray imaging means are rotated by the rotating means, a second sliding step of causing the sliding means to move the x-ray imaging means to a second detection position where the x-ray beam that passes through a second region of the object is detected, and a second imaging step of causing the x-ray imaging means to obtain a second set of projection images which goes through the second region while the x-ray source and the x-ray imaging means are rotated by the rotating means, and the image processing means executes a pasting-and-composing step of pasting and composing projection images among the first set of projection images and the second set of projection images, respectively, having the same phase angle of the supporting means, and the sliding means includes an origin-position detecting means for detecting an origin position of the x-ray imaging means, and the x-ray imaging means is moved linearly from the predetermined origin position to the first detection position and the second detection position, respectively, in the first sliding step and the second sliding step, and the origin-position detecting means includes a light blocking plate that is moved linearly together with the x-ray imaging means by the sliding means and an optical sensor that detects a position of an end of the light blocking plate, and a time point at which the end of the light blocking plate passes the optical sensor in a forward direction is detected as the origin position.

The "phase angle" of the supporting means in this specification means a rotational state of the supporting means viewed from an object that is represented by a rotation angle measured from an arbitrary reference position.

By causing the sliding means to move the x-ray imaging means linearly in a direction along the photo receiving surface, it becomes possible to secure a highly accurate movement precision of the x-ray imaging means in the first sliding step and the second sliding step.

Hence, since data processing may be performed by offsetting the x-ray imaging means with the traveled distance in the linear motion of the x-ray imaging means, it is possible to highly precisely paste the first set of projection images which is obtained at the first detection position and the second set of projection images which is obtained at the second detection position together.

Next, by reconfiguring the highly precise projection image which is obtained by pasting the first set of projection images and the second set of projection images together, it is possible to obtain an image having a large FOV which is covered by the first detection position of the x-ray imaging means and the second detection position thereof.

In this fashion, the present invention can provide the dental x-ray photographing device which is capable of obtaining a highly precise image while at the same time obtaining a large FOV using an inexpensive x-ray imaging means that has a narrow photo receiving surface.

Also, according to the present invention, by moving the x-ray imaging means from the predetermined origin position set to the first detection position and the second detection position, respectively, with reference to the origin position, a distance from the origin position to the first detection position and a distance from the origin position to the second detection position are managed, and thus a positional precision of the detection position is improved.

In the present invention, it is desirable that the rotation direction of the x-ray imaging means in the second imaging step should be opposite to that of the x-ray imaging means in the first imaging step.

According to such a configuration, by setting the rotation direction of the first imaging step to be opposite to that of the second imaging step, it is possible to reduce the operating time of the rotating means in a reciprocating image pickup.

It is desirable that the present invention should further include a set of sighting devices which allow visual checking of a level of mutual overlap of the set of sighting devices and which detect a difference in the phase angle between the rotation direction of the x-ray imaging means in the second imaging step and the rotation direction of the x-ray imaging means in the first imaging step.

According to such a configuration, by visually checking the level of mutual overlap, it is possible to detect and adjust the difference in the phase angle of the image pickup by the supporting means in the forward direction and in the reverse direction.

It is desirable that the present invention should further include an image pickup device that is for visually checking the level of overlap.

According to such a configuration, by having the image pickup device, it is possible to detect the difference in the phase angle objectively and to improve the detection precision, so that a correction is surely performed.

Effect of the Invention

The dental x-ray photographing device of the present invention is capable of obtaining a highly precise image while at the same time obtaining a large FOV using an inexpensive x-ray imaging means that has a narrow photo receiving surface.

BRIEF DESCRIPTION OF DRAWINGS

FIGS. 2(a) and 2(b) are each an explanatory diagram for a configuration of a sliding means according to the embodiment of the present invention, and FIG. 2A is a front view and FIG. 2B is a side view;

FIG. 3A is an (first) exemplary diagram explaining an operation when a first imaging step and a second imaging step are carried out in the same direction, and a portion (a) and a portion (b) are plan views showing a relationship between an object and an arm, and a portion (c) is a conceptual diagram showing a set of projection images;

FIG. 3B is a (second) diagram like FIG. 3A, and a portion (a) and a portion (b) are plan views;

FIG. 3C is a (third) diagram like FIG. 3A, and a portion (a) and a portion (b) are plan views and a portion (c) is a conceptual diagram;

FIG. 4A is an (first) exemplary diagram explaining an operation of when the first imaging step and the second imaging step are carried out in the opposite direction, and a portion (a) and a portion (b) are plan views showing a relationship between an object and an arm, and a portion (c) is a conceptual diagram showing a set of projection images;

FIG. 4B is a (second) diagram like FIG. 4A, and a portion (a) and a portion (b) are plan views;

FIG. 4C is a (third) diagram like FIG. 4A, and a portion (a) is a plan view, a portion (b) shows sets of picked up projection images, and a portion (c) is a conceptual diagram showing a set of projection images with the image pickup order reversed;

FIGS. 5A and 5B are each a diagram showing an attachment state of an angle-offset adjusting device when the first imaging step and the second imaging step are carried out in opposite directions, and FIG. 5A is a side view and FIG. 5B is an enlarged plan view of the adjusting tool; FIGS. 6A, 6B, and 6D are plan views, and FIGS. 6C and 6E are front views of the adjusting tool as viewed from a camera.

BEST MODE FOR CARRYING OUT THE INVENTION

A detailed explanation will be given of an embodiment of the present invention with reference to the accompanying drawings as needed.

Figure 1:
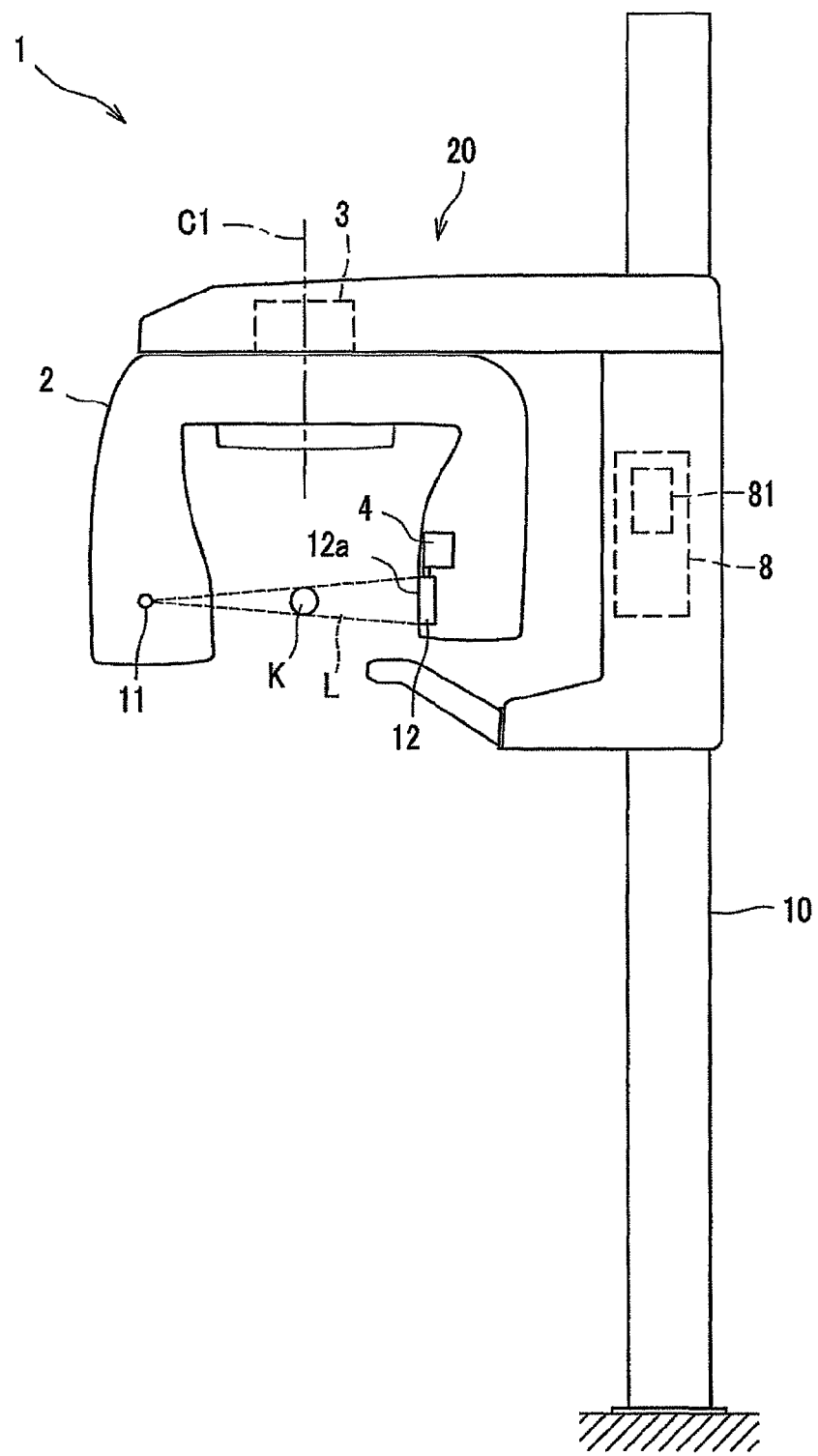
FIG. 1 is a side view showing a configuration of a dental x-ray photographing device according to an embodiment of the present invention.

A dental x-ray photographing device 1 according to an embodiment of the present invention includes, as shown in FIG. 1, a pole 10 and a main body 20 that is arranged on the pole 10 in a freely movable manner, and the main body 20 is provided with an arm 2 that is rotatable around the vertical axis.

In the dental x-ray photographing device 1, an object K is an unillustrated affected part of a patient, and the patient has his/her head fixed inwardly of the arm 2. With the object K being fixed, an x-ray image pickup is performed with the arm 2 rotated around the object K.

Although an explanation will be given of a case in which a CT tomographic image is obtained through an x-ray imaging means 12 in this embodiment, the present invention can be also applied to a cephalic radiographic device and a panoramic photographing device. Also, in order to cope with a positioning with respect to the object K and with various forms of image pickup, the arm 2 can be configured to be freely movable within a two-dimensional plane in the back-and-forth direction and in the horizontal direction through a movable table, etc., as needed.

As shown in FIG. 1, the dental x-ray photographing device 1 includes an x-ray source 11 that irradiates the object K with x-ray beam L, the x-ray imaging means 12 that detects the x-ray beam L which passes through the object K, the arm 2 that is a supporting means for supporting the x-ray source 11 and the x-ray imaging means 12, a rotating means 3 for rotating the arm 2 around an arm rotation center axis C1, a sliding means 4 for linearly moving the x-ray imaging means 12 in a direction along a photo receiving surface 12a, a control device 8 that controls the operation of the rotating means 3 and that of the sliding means 4, and an image processing means 81 for processing a projection image picked up by the x-ray imaging means 12.

The x-ray source 11 and the x-ray imaging means 12 are arranged on the arm 2 so as to face with each other with the object K being present therebetween. The arm 2 is rotated by the rotating means 3 like a servo motor, the x-ray source 11 and the x-ray imaging means 12 are rotated around the object K, and the x-ray beam L which is emitted from the x-ray source 11 and passes through the object K is detect by the x-ray imaging means 12.

As shown in FIG. 2A, the x-ray imaging means 12 is a plane sensor with the rectangular photo receiving surface 12a, which is, for example, a CMOS sensor, a CCD sensor, CdTe sensor, and other imaging sensors.

As shown in FIG. 2, the sliding means 4 includes a ball screw 41, a driving motor 42 that rotates the ball screw 41, a nut 43 that is threaded with the ball screw 41, a holder 44 that is fixed to the nut 43, the x-ray imaging means 12 that is fixed to the holder 44, a linear movement guide 45 that supports the x-ray imaging means 12 so as to be able to reciprocate in the direction along the photo receiving surface 12a, and an origin-position detecting means 5 for detecting an origin position P0 (see FIG. 3A(a)) of the x-ray imaging means 12 (the photo receiving surface 12a).

As shown in FIG. 2, the origin-position detecting means 5 includes a light blocking plate 51 that is fixed to the nut 43, and an optical sensor 52 that detects a position of an end 51a of the light blocking plate 51. When the nut 43 moves in a forward direction A, the origin-position detecting means 5 detects, as the origin position P0 (see FIG. 3A(a)) of the photo receiving surface 12a of the x-ray imaging means 12, a time point at which the end 51a of the light blocking plate 51 passes the optical sensor 52 in the forward direction A.

Next, the control means 8 (see FIG. 1) linearly moves the x-ray imaging means 12 in the horizontal direction within the arm 2 through the sliding means 4 until the photo receiving surface 12a reaches a first detection position P1 (see FIG. 3A(a)) from the origin position P0 (see FIG. 3A(a)), and a second detection position P2 (see FIG. 3B(b)) from the origin position P0.

According to such a configuration, it is possible to obtain a wide-range FOV which is covered by an FOV that is obtained from the photo receiving surface 12a at the first detection position P1 and an FOV that is obtained from the photo receiving surface 12a at the second detection position P2.

Regarding the operation of the dental x-ray photographing device 1 employing the above-explained configuration, a first embodiment (see FIGS. 3A through 3D), and a second embodiment (see FIGS. 4A through 4D) will be explained.

Note that in FIG. 3 and FIG. 4, for the convenience sake of the explanation, a conceptual expression that the photo receiving surface 12a of the x-ray imaging means 12 moves is given.

In the first embodiment (see FIG. 3A through FIG. 3D), a first imaging step and a second imaging step are performed while the arm 2 is rotated in the same direction, but the second embodiment (see FIG. 4A through FIG. 4D) differs from the first embodiment in that the rotation direction of the arm 2 in the first imaging step and the rotation direction thereof in the second imaging step are opposite.

The first embodiment and the second embodiment equally obtain a set of projection images when the x-ray imaging means 12 is located at the first detection position P1 and at the second detection position P2, respectively.

In other words, the image pickup region of the object K is conceptually divided into two regions, and with the x-ray imaging means 12 located at positions corresponding to respective regions, the set of projection images are obtained, and the set of projection images are correspondingly composed one another in order to perform CT reconfiguration.

In the first embodiment, the control device 8 executes a first sliding step (see FIG. 3A(a)) of moving the x-ray imaging means from the origin position (P0) to the first detection position (P1), a first imaging step (see FIG. 3A(b) through FIG. 3A(c)) of obtaining a first set of projection images R1 to R190 which go through the first region of the object by causing the rotating means 3 to rotate the arm 2 by 190 degrees counterclockwise, a step (see FIG. 3B(a)) of rotating the arm 2 clockwise while returning the x-ray imaging means 12 from the first detection position P1 to the origin position P0 by the sliding means 4 to return the x-ray imaging means 12 and the x-ray source 11 back to an original position (an image pickup start position in the first imaging step, a reference position) that is shown in FIG. 3B(a), a second sliding step (see FIG. 3B(b)) of moving the x-ray imaging means 12 from the origin position (P0) to the second detection position (P2), and a second imaging step (see FIG. 3A(a) through FIG. 3A(c)) of causing the rotating means 3 to rotate the arm 2 counterclockwise by 190 degrees and of obtaining a second set of projection images L1 to L190 which go through the second region of the object K.

Next, the image processing means 81 executes a pasting-and-composing step of pasting and composing each of the first set of projection images R1 to R190 and each of the second set of projection images L1 to L190 having the same phase angle of the arm 2.

As shown in FIG. 3A(a), the first sliding step is a step of moving the photo receiving surface 12a of the x-ray imaging means 12 from the origin position P0 to the first detection position P1 using the sliding means 4 (see FIG. 2).

Note that it is not necessary to rotate the arm 2 in the first sliding step, but it is possible to slide the photo receiving surface while the arm 2 is being rotated since rotation of the arm 2 does not affect the sliding step.

As shown in FIG. 3A(c), in the first imaging step, the first set of projection images R1 to R190 is the set of 190 projection images picked up with one degree intervals in the rotation of the arm 2 by 190 degrees from the reference position (origin) shown in FIG. 3A(a).

In this embodiment, the rotation angle of the arm 2 is set to be 190 degrees that is equal to or greater than 180 degrees in consideration of an x-ray glancing angle from 180 degrees in the case of a half reconstruction, but if the x-ray glancing angle does not have to be considered, the rotation angle of the arm 2 may be 180 degrees, and likewise in the case of a full reconstruction, the rotation angle may be 360 degrees or greater.

The first region of the object K is a region of the object K that corresponds to a range where the x-ray beam L moves from FIG. 3A(a) to FIG. 3A(b), and in this first region, the photo receiving surface 12a of the x-ray imaging means 12 is present at the first detection position P1.

The region of the object K means a region of the object K, through which the rotating x-ray beam L emitted from the x-ray source 11 passes, but it is a merely conceptual region and does not mean any specific region of the object K.

In the step of returning the x-ray imaging means 12 and the x-ray source 11 to the original position (the reference position) shown in FIG. 3A(a) while returning the x-ray imaging means 12 to the origin position P0, the sliding means 4 and the arm 2 are operated simultaneously, but the present invention is not limited to this configuration, and the sliding of the sliding means 4 and the rotation of the arm 2 may be executed individually.

As shown in FIG. 3B(b), the second sliding step is a step of moving the photo receiving surface 12a of the x-ray imaging means 12 from the origin position P0 to the second detection position P2 using the sliding means 4 (see FIG. 2).

In this embodiment, the second sliding step is executed after the step of returning to the original position, but the second sliding step may be executed while the return operation to the original position is being executed, or the step of returning to the original position may be executed after the second sliding step.

In short, it is appropriate if the step of returning to the original position and the second sliding step complete before the second imaging step is executed.

As shown in FIGS. 3C(a) to 3C(c), in the second imaging step, with the x-ray imaging means 12 being located at the second detection position P2, the arm 2 is rotated by the rotating means 3 counterclockwise by 190 degrees like the first imaging step, and the second set of projection images L1 to L190 that go through the second region of the object K are obtained.

The second region of the object K is a region that corresponds to a range where the x-ray beam L moves from FIG. 3C(a) to FIG. 3C(b), and in this second region, the photo receiving surface 12a of the x-ray imaging means 12 is located at the second detection position P2 (see FIG. 3C(a)).

In the pasting-and-composing step, since the first set of projection images R1 to R190 and the second set of projection images L1 to L190 are the sets of images picked up in the same way by rotating the arm 2 in the same direction by 190 degrees counterclockwise from the same reference position shown in FIG. 3(a), the projection images R1 and L1 have the same phase angle, and likewise, up to the projection images R190 and L190 in the order of image pickup, the phase angles remain the same.

Figure 3D:
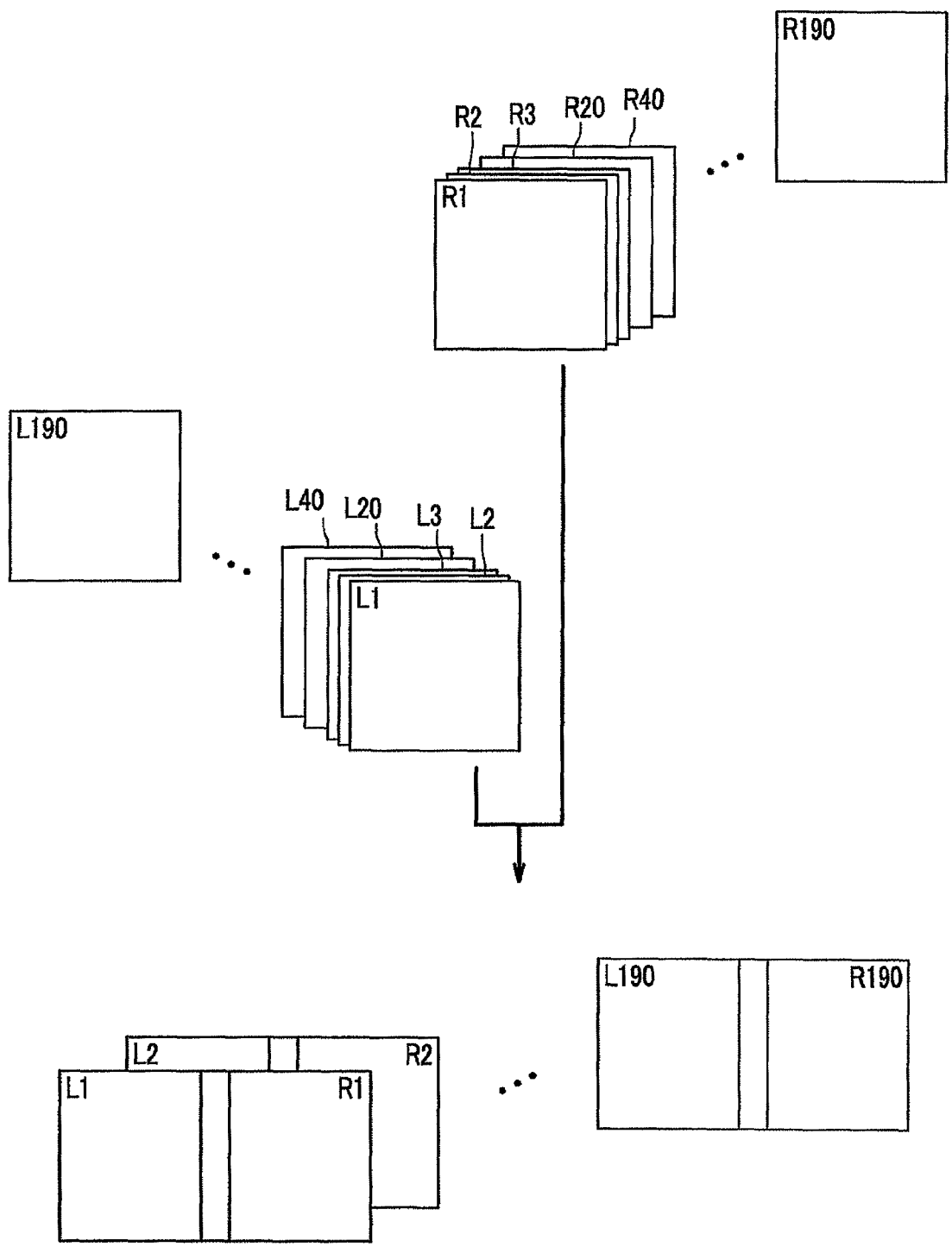
FIG. 3D is a (fourth) diagram like FIG. 3A, and is a conceptual diagram showing a concept of pasting and composing.

Hence, in the pasting-and-composing step of this embodiment, as shown in FIG. 3D, the projection images from R1 and L1 to the projection images R190 and L190 that have the same phase angle are correspondingly offset by a predetermined amount, superimposed, and composed together.

Next, highly precise projection images obtained by pasting the first set of projection images R1 to R190 with the second set of projection images L1 to L190 are subjected to a CT reconstruction, so that a CT tomographic image is obtained which has a wide-range FOV that is covered by the first detection position P1 of the x-ray imaging means 12 and the second detection position P2 thereof.

Subsequently, an explanation will be given of the second embodiment in which the rotation direction of the arm 2 in the first imaging step and the rotation direction thereof in the second imaging step are opposite with reference to FIG. 4A through FIG. 4D.

In the second embodiment, the control device 8 executes a first sliding step (see FIG. 4A(a)) of moving the x-ray imaging means 12 from the origin position (P0) to the first detection position (P1), a first imaging step (see FIG. 4A(b) and FIG. 4A(c)) of causing the rotating means 3 to rotate the arm 2 by 190 degrees counterclockwise and of obtaining the first set of projection images R1 to R190 which go through the first region of the object K, a step (see FIG. 4B(a)) of returning the x-ray imaging means 12 from the first detection position P1 to the origin position P0 by the sliding means 4, the second sliding step (see FIG. 4B(b)) of moving the x-ray imaging means 12 from the origin position P0 to the second detection position P2, and a second imaging step (see FIG. 4C(c)) of causing the rotating means 3 to rotate the arm 2 clockwise by 190 degrees and of obtaining and rearranging the second set of projection images L1 to L190 (see FIG. 4C(a) and 4C(b)) which go through the second region of the object K.

As shown in FIG. 4A, the second embodiment has the same first sliding step (see FIG. 4A(a)) and first imaging step (see FIG. 4A(b) and FIG. 4A(c)) as those of the first embodiment, so that the duplicated explanation will be omitted.

In the second embodiment, since the rotation direction (clockwise) of the x-ray imaging means 12 in the second imaging step is opposite to that (counterclockwise) thereof in the first imaging step, the second set of projection images L1 to L190 is obtained which go through the second region of the object K while the arm 2 is tracing the same trajectory and returned to the original position shown in FIG. 4C(a) after the first imaging step is executed.

The first set of projection images R1 to R190 are images picked up while the arm is rotated by 190 degrees counterclockwise from the reference position shown in FIG. 4A(a). On the other hand, the second set of projection images L1 to L190 are images picked up while the arm is rotated in the opposite direction clockwise from a state, as a start point, into which the arm has been rotated by 190 degrees counterclockwise from the reference position shown in FIG. 4A(a), to the reference position shown in FIG. 4C(a).

Hence, the second set of projection images L1 to L190 have the same phase angle as that of the first set of projection images R1 to R190 when the second set of projection images are re-arranged in a reverse image pickup order from L190 to L1 (see FIG. 4C(b) and FIG. 4C(c)).

Figure 4D:
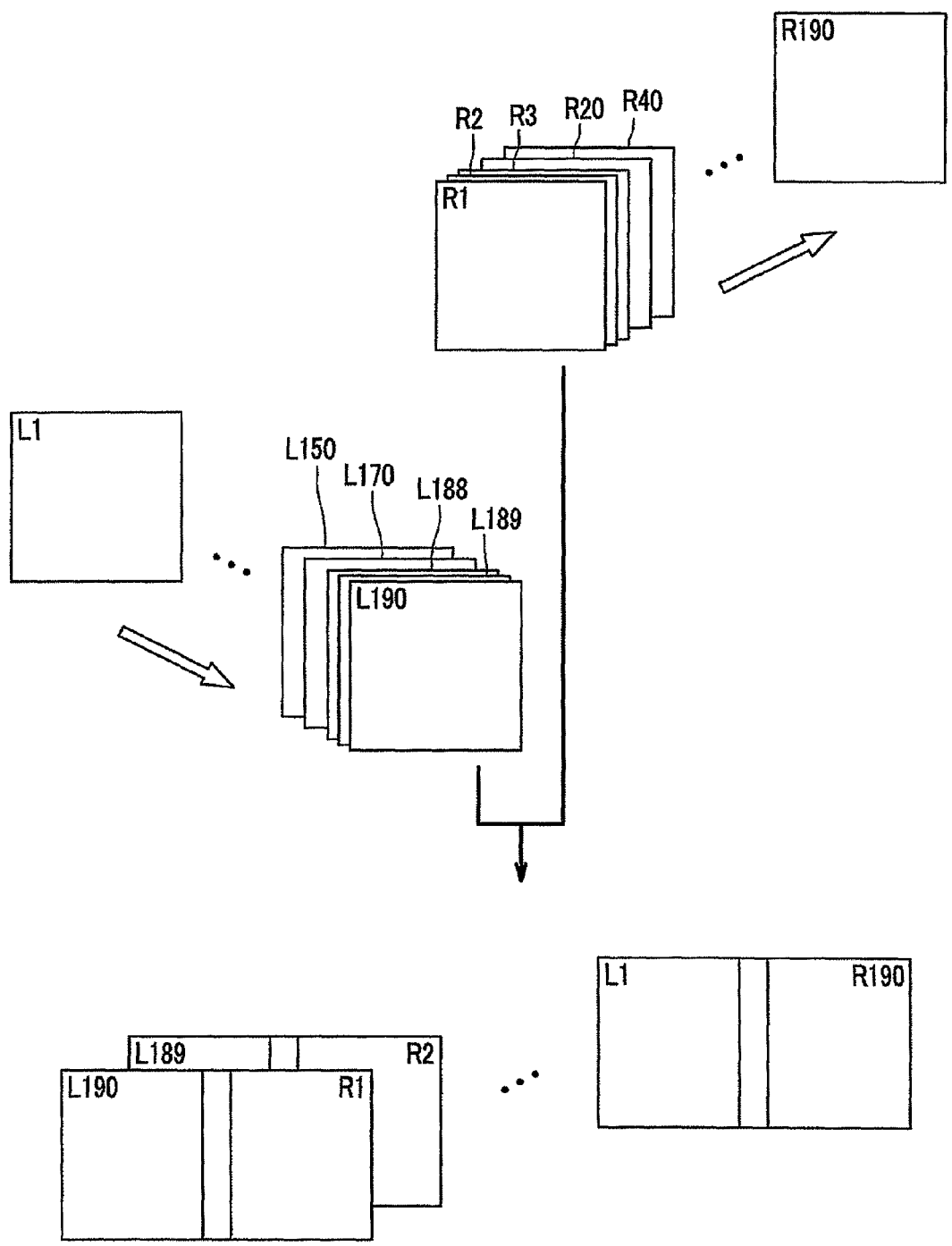
FIG. 4D is a (fourth) diagram like FIG. 4A, and is a conceptual diagram showing a concept of pasting and composing.

In the pasting-and-composing step according to the second embodiment, as shown in FIG. 4D, projection images having same phase angles from the projection images R1 and L190 to the projection images R190 and L1 are composed correspondingly to one another through the above-explained rearrangement.

Figure 6:
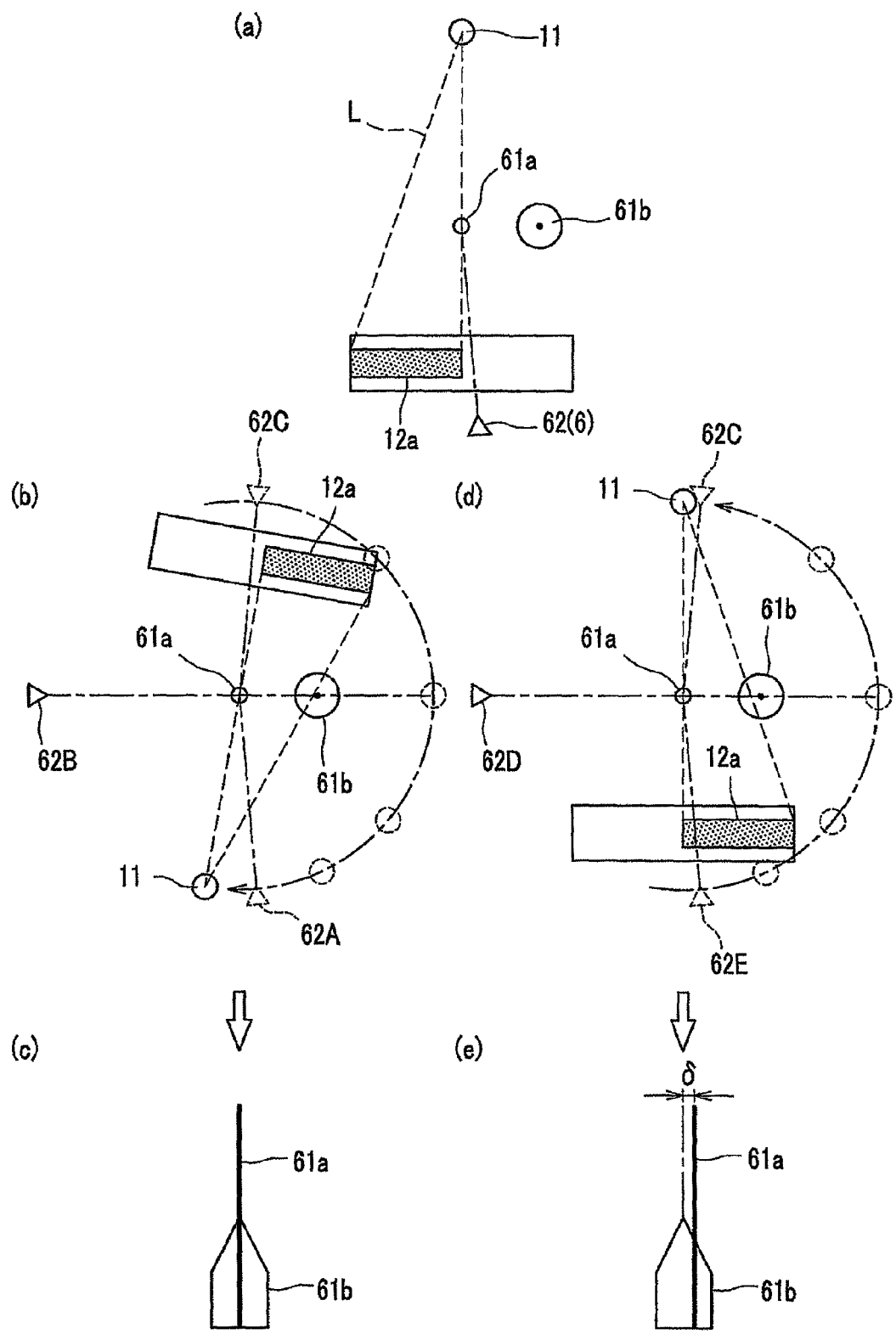
FIGS. 6A to 6E are explanatory diagrams illustrating an adjusting method of an angle-offset when the first imaging step and the second imaging step are in the opposite direction.

Next, an explanation will be given of an angle-offset adjusting device when the first imaging step and the second imaging step are in the opposite direction with reference to FIG. 5 and FIG. 6. Note that the configurations other than the angle-offset adjusting device are the same as those of the above-explained embodiment, so that the same reference numerals are given to the same structural elements, and the duplicated explanation thereof will be omitted.

First Example

As shown in FIG. 5, an angle-offset adjusting device 6 includes an adjusting tool 61 for visually recognizing the level of mutual overlap of projection images and detecting a difference in the phase angle between the rotation direction of the x-ray imaging means 12 in the second imaging step and the rotation direction of the x-ray imaging means 12 in the first imaging step.

The adjusting tool 61 includes a cylindrical needle member 61a and a pyramid-like or conical convex member 61b that enables visual recognition of the overlap with the needle member 61a which are a set of sighting devices and which are arranged at the rotation center of the arm 2, and a base member 61c which can attach the needle member 61a and the convex member 61b to a bite block 20a. Also, the adjusting tool 61 is attached to the bite block 20a of the main body 20 in a detachable manner.

According to such a configuration, the angle-offset adjusting device 6 causes the x-ray source 11 to emit x-rays, and allows a user to visually check the projection images with the same phase angle, e.g., 95th projection image in the forward direction and 95th projection image in the reverse direction, thereby correcting the misalignment of the arm 2 in the forward rotation direction (see FIG. 6B) and in the reverse rotation direction (see FIG. 6D).

Note that in this embodiment, the needle member 61a and the convex member 61b are used as a set of sighting devices, but the present invention is not limited to this configuration, and a concaved member or simply a flat plate that has a drawing pattern as a marking, etc., can be used as long as it enables visual recognition of the level of mutual overlap.

Second Example

As shown in FIG. 5, a second example employs a configuration that further includes, in addition to the configuration of the first example, a camera 62 (see FIG. 6A) that is an image pickup device which visually checks the level of the overlap of the cylindrical needle member 61a and the pyramid-like or conical convex member 61b.

The camera 62 is attached to a predetermined location in the arm 2 (behind the x-ray imaging means 12), but when 190 projection images are picked up, it is preferred that the camera should be provided at a position where the projection images having the same phase angle, e.g., 95th projection image that is the middle of the set of projection images, is visually checked.

According to such a configuration, the angle-offset adjusting device 6 causes the camera 62 to visually checking the level of the overlap of the needle member 61a and the convex member 61b (misalignment δ, see FIG. 6E) at the same position (a position where the needle member 61a and the convex member 61b overlap with each other) in the opposite rotation directions those are the forward direction (see FIG. 6D) and the reverse direction (see FIG. 6D), thereby detecting and collecting the misalignment of the arm 2 in the forward rotation direction and in the reverse rotation direction.

More specifically, when the arm 2 is rotated clockwise (forward direction) by 190 degrees from the reference position shown in FIG. 6A, the camera 62 is moved from a position of 62A shown in FIG. 6B, goes through a position of 62B for visually checking the level of the overlap (misalignment δ) of the needle member 61a with the convex member 61b, and is moved to a position of 62C.

Likewise, when the arm 2 is rotated counterclockwise (reverse direction) by 190 degrees from the position of 62C at this time (reverse), the camera 62 goes through a position of 62D for visually checking the level of the overlap (misalignment δ) of the needle member 61a with the convex member 61b and is moved to a position of 62E.

In this fashion, by visually checking the level of the overlap (misalignment δ) of the needle member 61a with the convex member 61b through the camera 62 at the same position, i.e., the position 62B of FIG. 6B and the position 62D of FIG. 6D, it becomes possible to detect and adjust the difference in the phase angle of the arm 2 in the forward direction and in the reverse direction.

Note that in this embodiment, since the needle member 61a that can be visually recognized easily and the convex member 61b are used, it is possible to adjust the angle-offset by performing image recognition on the picked up images. For example, the horizontal position of the needle member 61a and that of the convex member 61b are recognized and adjusted by pattern matching.

Although the embodiments of the present invention were explained above, the present invention is not limited to the above-described embodiments and can be changed and modified as needed.

For example, the sliding means 4 according to the above-explained embodiments moves in the horizontal direction, but when it is moved in the vertical direction, the FOV of the x-ray imaging means 12 can be enlarged in the vertical direction. Also, in the above-explained embodiments, the region of the object K is divided into two regions, and the x-ray imaging means 12 is moved to the first detection position P1 and the second detection position P1 correspondingly to these two regions. However, the region of the object K may be divided into equal to or more than three regions and the x-ray imaging means 12 may be moved correspondingly to respective regions.

Also, in the above-explained embodiments, each projection image of the first set of the projection images R1 to R190 and each projection image of the second set of projection images L1 to L190 are superimposed and composed together, but a composed image can be generated by merely arranging the projection images so that respective ends thereof are joined together, not by superimposing those as long as the precision of the movement of the x-ray imaging means 12 in a linear movement means is secured.

In the above-explained embodiments, in consideration of the moving time, the first detection position P1 is set to be more distant from the origin position P0 in comparison with the second detection position P2. However, it is possible to set the first detection position P1 to be closer to the origin position P0 in comparison with the second detection position P2.

Also, regarding the rotation direction of the arm 2 in the imaging step of the above-explained embodiments, the images are picked up while the arm is rotated counterclockwise in the first embodiment, but the images may be picked up clockwise as long as it is in the same direction. Also in the second embodiment, the forward rotation direction and the reverse rotation direction may be reversed, and the images may be picked up while the arm is rotated clockwise in the forward direction and is rotated counterclockwise in the reverse direction.

DESCRIPTION OF REFERENCE NUMERALS

1 Dental x-ray photographing device
2 Arm (supporting means)
3 Rotating means
4 Sliding means
5 Origin-position detecting means
6 Angle-offset adjusting device
12 X-ray imaging means
12a Photo receiving surface
61 Adjusting tool
61a Needle member (sighting member)
61b Convex member (sighting member)
62 Camera (image pickup means)
K Object
L X-ray beam
P0 Origin position
P1 First detection position
P2 Second detection position
R1 to R190 Set of projection images
L1 to L190 Set of projection images

The invention claimed is:

1. A dental x-ray photographing device comprising:
an x-ray source that emits x-ray beam to an object;
an x-ray imaging means for detecting the x-ray beam which is emitted from the x-ray source and passes through the object;
a supporting means for supporting the x-ray source and the x-ray imaging means;
a rotating means for rotating the supporting means around a vertical axis to rotate the x-ray source and the x-ray imaging means around the object in a horizontal direction;
a sliding means for linearly moving the x-ray imaging means in a direction along a photo receiving surface;
a control device that controls an operation of the rotating means and an operation of the sliding means; and
an image processing means for processing a projection image which is obtained by the x-ray imaging means, wherein
the control device executes:
a first sliding step of causing the sliding means to move the x-ray imaging means to a first detection position where the x-ray beam that passes through a first region of the object is detected;
a first imaging step of causing the x-ray imaging means to obtain a first set of projection images which go through the first region while the x-ray source and the x-ray imaging means are rotated by the rotating means;
a second sliding step of causing the sliding means to move the x-ray imaging means to a second detection position where the x-ray beam that passes through a second region of the object is detected; and
a second imaging step of causing the x-ray imaging means to obtain a second set of projection images which goes through the second region while the x-ray source and the x-ray imaging means are rotated by the rotating means,
the image processing means executes a pasting-and-composing step of pasting and composing projection images among the first set of projection images and the second set of projection images, respectively, having the same phase angle of the supporting means,
the sliding means comprises origin-position detecting means for detecting an origin position of the x-ray imaging means,
the x-ray imaging means is moved linearly from the predetermined origin position to the first detection position and the second detection position, respectively, in the first sliding step and the second sliding step,
the origin-position detecting means comprises:
a light blocking plate that is moved linearly together with the x-ray imaging means by the sliding means; and
an optical sensor that detects a position of an end of the light blocking plate, and
a time point at which the end of the light blocking plate passes the optical sensor in a forward direction is detected as the origin position.

2. The dental x-ray photographing device according to claim 1, wherein a rotation direction of the x-ray imaging means in the second imaging step is opposite to that of the x-ray imaging means in the first imaging step.

3. The dental x-ray photographing device according to claim 2, further comprising a set of sighting devices which allow visual checking of a level of mutual overlap of the set of sighting devices and which detect a difference in the phase angle between the rotation direction of the x-ray imaging means in the second imaging step and the rotation direction of the x-ray imaging means in the first imaging step.

4. The dental x-ray photographing device according to claim 3, further comprising an image pickup device that is for visually checking the level of overlap.

* * * * *